United States Patent
Chuang et al.

(10) Patent No.: US 10,364,162 B2
(45) Date of Patent: Jul. 30, 2019

(54) SYSTEM AND METHOD FOR TREATING SALT-CONTAINING GLYCERIN WASTEWATER

(71) Applicants: National Tsing Hua University, Hsinchu (TW); Chang Chun Plastics Co., Ltd., Taipei (TW); Chang Chun Petrochemical Co., Ltd., Taipei (TW)

(72) Inventors: Shih-Cheng Chuang, Hsinchu (TW); Shi-Shang Jang, Hsinchu (TW); David S. H. Wong, Hsinchu (TW); Sheng-Chieh Wang, Hsinchu (TW); En-Ko Lee, Hsinchu (TW)

(73) Assignees: National Tsing Hua University, Hsinchu (TW); Chang Chun Plastics Co., Ltd., Taipei (TW); Chang Chun Petrochemical Co., Ltd., Taipei (TW)

( * ) Notice: Subject to any disclaimer, the term of this patent is extended or adjusted under 35 U.S.C. 154(b) by 5 days.

(21) Appl. No.: 15/672,304

(22) Filed: Aug. 9, 2017

(65) Prior Publication Data

US 2019/0002305 A1  Jan. 3, 2019

(30) Foreign Application Priority Data

Jun. 30, 2017 (TW) .............................. 106121927 A

(51) Int. Cl.
*C02F 1/04* (2006.01)
*C02F 1/00* (2006.01)
(Continued)

(52) U.S. Cl.
CPC ................ *C02F 1/04* (2013.01); *B01D 3/143* (2013.01); *B01L 3/00* (2013.01); *C02F 1/001* (2013.01);
(Continued)

(58) Field of Classification Search
CPC ..... C02F 1/00; C02F 1/001; C02F 1/04; C07C 29/80
See application file for complete search history.

(56) References Cited

U.S. PATENT DOCUMENTS 4,164,507 A    8/1979  Blytas et al.
2009/0275726 A1*  11/2009  Krafft ..................... C07C 29/62
                                                                528/421

FOREIGN PATENT DOCUMENTS

CN    1004695      7/1989
CN    102503014    6/2012
(Continued)

OTHER PUBLICATIONS

"Office Action of Taiwan Counterpart Application", dated Apr. 23, 2018, p. 1-p. 9.
(Continued)

*Primary Examiner* — Brian A McCaig
(74) *Attorney, Agent, or Firm* — JCIPRNET

(57) ABSTRACT

A system and a method for treating salt-containing glycerin wastewater are provided, wherein the system for treating the salt-containing glycerin wastewater includes a mixing tank, a filtering device, a distillation column, and a water supply device. The mixing tank is adapted to mix salt-containing glycerin wastewater with a concentrated hydrochloric acid to obtain a mixture. The filtering device communicates with the mixing tank and filters the mixture to obtain an acidic filtrate and a precipitated salt. The distillation column communicates with the filtering device and receives the acidic filtrate from the filtering device. The water supply device supplies water to the acidic filtrate. The system and method for treating the salt-containing glycerin wastewater can effectively recycle hydrochloric acid.

10 Claims, 5 Drawing Sheets

(51) Int. Cl.
*C02F 1/66* (2006.01)
*B01D 3/14* (2006.01)
*C07C 29/80* (2006.01)
*B01L 3/00* (2006.01)
B01D 3/00 (2006.01)
C02F 101/34 (2006.01)
C02F 103/38 (2006.01)

(52) U.S. Cl.
CPC ............... *C02F 1/66* (2013.01); *C07C 29/80* (2013.01); *C02F 2101/345* (2013.01); *C02F 2103/38* (2013.01)

(56) References Cited

FOREIGN PATENT DOCUMENTS

| CN | 102557164 | 7/2012 |
|---|---|---|
| CN | 102689936 | 9/2012 |
| CN | 104230083 | 12/2014 |
| CN | 104230084 | 12/2014 |
| CN | 105645624 | 6/2016 |
| TW | 574059 | 2/2004 |

OTHER PUBLICATIONS

S. Carrà et al.,"Synthesis of Epichlorohydrin by Elimination of Hydrogen Chloride from Chlorohydrins. 1. Kinetic Aspects of the Process", Ind. Eng. Chem. Process Des. Dev., vol. 18, No. 3, Jul. 1979,pp. 424-427.
L. Ma et al.,"Synthesis of Epichlorohydrin From Dichloropropanols Kinetic Aspects of the Process", Chemical Engineering Research and Design,Transactions of the Inst,vol. 85,Issue A12, Dec. 2007, pp. 1580-1585.
Zong Min et al.,"Synthesis of Epichlorohydrin", Speciality Petrochemicals, vol. 24, Issue 5, Sep. 2007,pp. 32-35.
Jon Van Gerpen, "Biodiesel processing and production", Fuel Processing Technology,vol. 86,Issue 10,Jun. 2005, pp. 1097-1107.
Wenlei Xie et al.,"Transesterification of soybean oil catalyzed by potassium loaded on alumina as a solid-base catalyst", Applied Catalysis A: General, vol. 300, Issue 1, Jan. 20, 2006,pp. 67-74.
Sang Hee Lee et al.,"Direct preparation of dichloropropanol (DCP) from glycerol using heteropolyacid (HPA) catalysts: A catalyst screen study", Catalysis Communications, vol. 9, May 15, 2008, pp. 1920-1923.

* cited by examiner

SYSTEM AND METHOD FOR TREATING SALT-CONTAINING GLYCERIN WASTEWATER

CROSS-REFERENCE TO RELATED APPLICATION

This application claims the priority benefit of Taiwan application serial no. 106121927, filed on Jun. 30, 2017. The entirety of the above-mentioned patent application is hereby incorporated by reference herein and made a part of this specification.

BACKGROUND OF THE INVENTION

Field of the Invention

The invention relates to a system and a method for treating wastewater and more particularly relates to a system and a method for treating salt-containing glycerin wastewater.

Description of Related Art

In the process of producing many chemical materials, glycerin wastewater that contains more salt may be generated. For example, epichlorohydrin is the most important raw material for synthesis of epoxy resin, and epoxy resin is mainly used in the fields of coating, laminated board (printed circuit board), adhesive agent, civil construction, composite material, and so on. However, when glycerin is used to produce epichlorohydrin, glycerin wastewater that contains more salt is produced, and the by-products include glycerin, water, salt, and glycerin polymers.

In the existing techniques, an excess of concentrated hydrochloric acid is often used to treat the salt-containing glycerin wastewater to precipitate the salt. However, how to effectively recycle the hydrochloric acid remains an issue in this field.

SUMMARY OF THE INVENTION

The invention provides a system and a method for treating salt-containing glycerin wastewater for effectively recycling hydrochloric acid.

The invention provides a salt-containing glycerin wastewater treating system, which includes a mixing tank, a filtering device, a distillation column, and a water supply device. The mixing tank is adapted to mix salt-containing glycerin wastewater with a concentrated hydrochloric acid to obtain a mixture. The filtering device communicates with the mixing tank and filters the mixture to obtain an acidic filtrate and a precipitated salt. The distillation column communicates with the filtering device and receives the acidic filtrate from the filtering device. The water supply device supplies water to the acidic filtrate.

According to an embodiment of the invention, the salt-containing glycerin wastewater treating system further includes a salt-containing glycerin wastewater supply device and a concentrated hydrochloric acid supply device. The salt-containing glycerin wastewater supply device communicates with the mixing tank. The concentrated hydrochloric acid supply device communicates with the mixing tank.

According to an embodiment of the invention, in the salt-containing glycerin wastewater treating system, a concentration of the concentrated hydrochloric acid is 30% to 37%, for example.

According to an embodiment of the invention, in the salt-containing glycerin wastewater treating system, an amount of the concentrated hydrochloric acid is 0.5 to 1.5 times an amount of the salt-containing glycerin wastewater, for example.

According to an embodiment of the invention, in the salt-containing glycerin wastewater treating system, an amount of the water supplied to the acidic filtrate is 0.25 to 1 times an amount of the salt-containing glycerin wastewater, for example.

According to an embodiment of the invention, in the salt-containing glycerin wastewater treating system, the water supply device may communicate with an acidic filtrate storage tank that communicates between the filtering device and the distillation column, may communicate with an acidic filtrate delivery pipe that communicates between the filtering device and the distillation column, or may directly communicate with the distillation column.

According to an embodiment of the invention, the salt-containing glycerin wastewater treating system further includes a column top product storage tank. The column top product storage tank communicates with the distillation column and stores a column top product of the distillation column. The column top product includes a hydrochloric acid aqueous solution.

According to an embodiment of the invention, the salt-containing glycerin wastewater treating system further includes a hydrochloric acid gas supply device. The hydrochloric acid gas supply device communicates with the column top product storage tank.

According to an embodiment of the invention, the salt-containing glycerin wastewater treating system further includes a return pipe. The return pipe communicates between the column top product storage tank and the mixing tank.

The invention provides a salt-containing glycerin wastewater treating method, including: mixing a concentrated hydrochloric acid with salt-containing glycerin wastewater and performing salt precipitation to obtain a mixture; filtering the mixture to obtain an acidic filtrate and a precipitated salt; supplying water to the acidic filtrate; and distilling the acidic filtrate diluted with the water to separate a hydrochloric acid aqueous solution and glycerin wastewater.

According to an embodiment of the invention, in the salt-containing glycerin wastewater treating method, a concentration of the concentrated hydrochloric acid is 30% to 37%, for example.

According to an embodiment of the invention, in the salt-containing glycerin wastewater treating method, an amount of the concentrated hydrochloric acid is 0.5 to 1.5 times an amount of the salt-containing glycerin wastewater, for example.

According to an embodiment of the invention, in the salt-containing glycerin wastewater treating method, an amount of the water supplied to the acidic filtrate is 0.25 to 1 times an amount of the salt-containing glycerin wastewater, for example.

According to an embodiment of the invention, in the salt-containing glycerin wastewater treating method, a method of supplying the water to the acidic filtrate is supplying the water to an acidic filtrate storage tank, supplying the water to an acidic filtrate delivery pipe, or directly supplying the water to a distillation column that is adapted to distill the acidic filtrate, for example.

According to an embodiment of the invention, the salt-containing glycerin wastewater treating method further includes introducing a hydrochloric acid gas to the hydrochloric acid aqueous solution.

According to an embodiment of the invention, the salt-containing glycerin wastewater treating method further includes recycling the hydrochloric acid aqueous solution.

Based on the above, in the salt-containing glycerin wastewater treating system and method of the invention, concentrated hydrochloric acid is used to cause salt precipitation in the salt-containing glycerin wastewater, and therefore, salt is precipitated from the salt-containing glycerin wastewater effectively. In addition, since water is added to the acidic filtrate obtained through filtering, after the acidic filtrate diluted with water is distilled, the hydrochloric acid may be recycled effectively.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
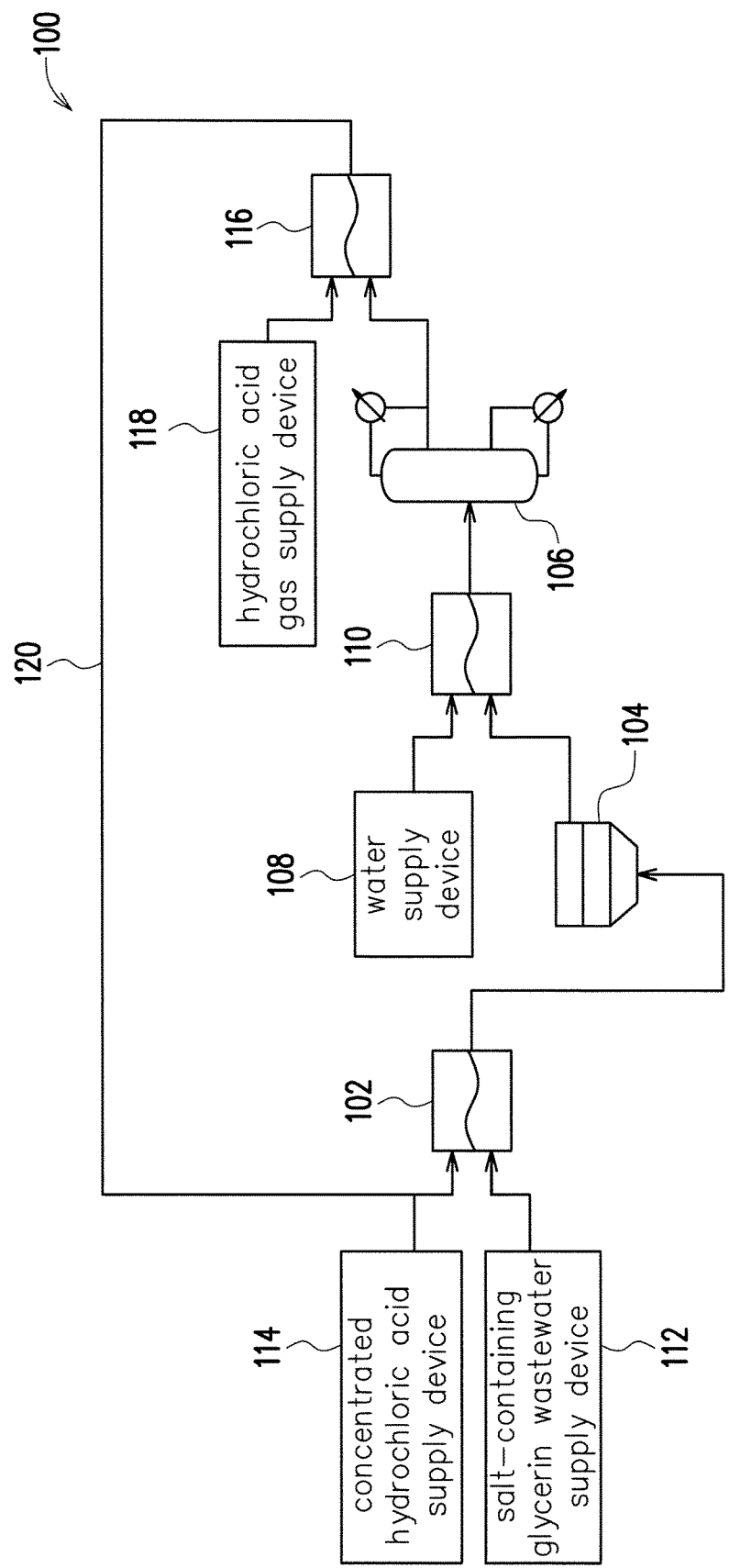
FIG. 1 is a schematic diagram of a salt-containing glycerin wastewater treating system according to an embodiment of the invention.
Figure 2:
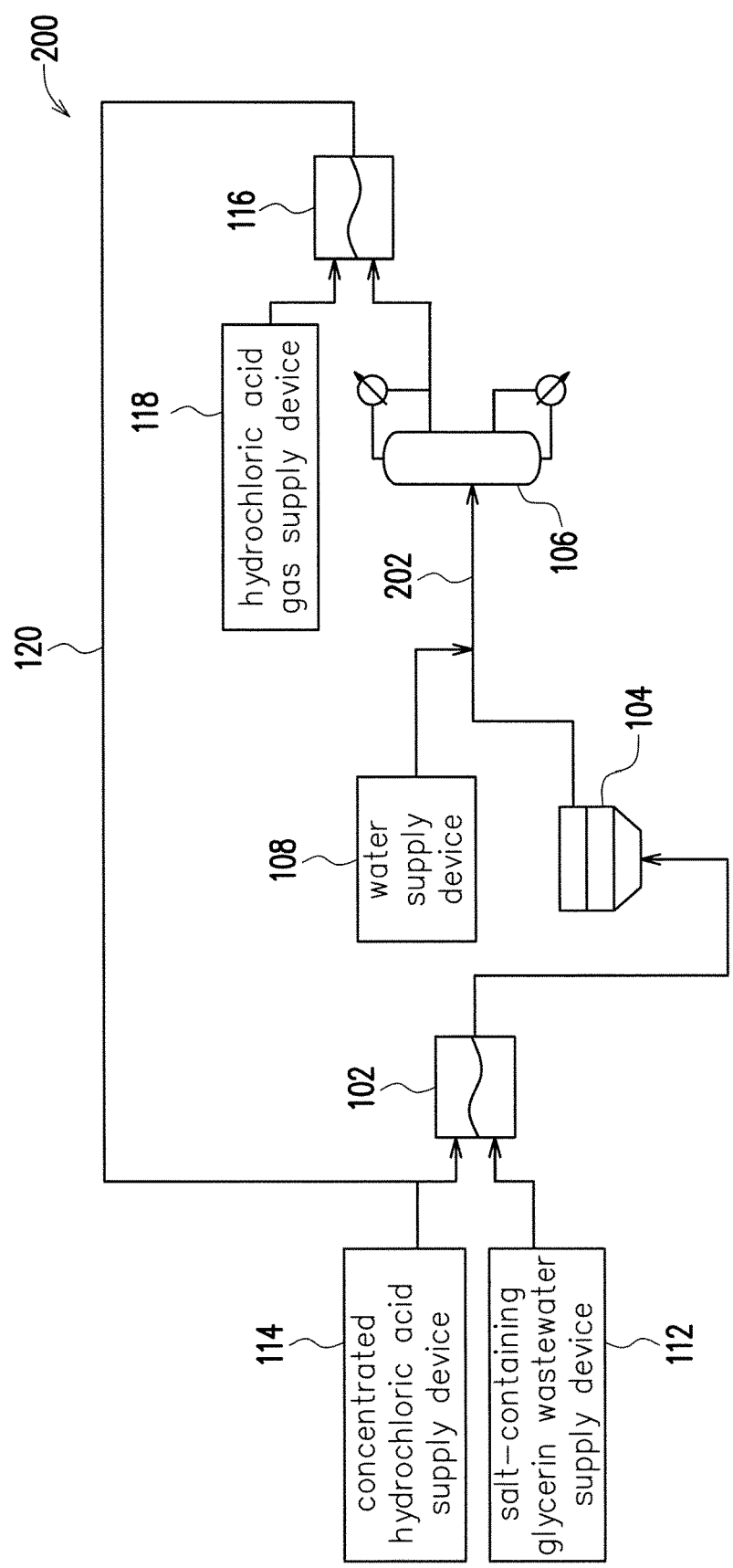
FIG. 2 is a schematic diagram of the salt-containing glycerin wastewater treating system according to another embodiment of the invention.
Figure 3:
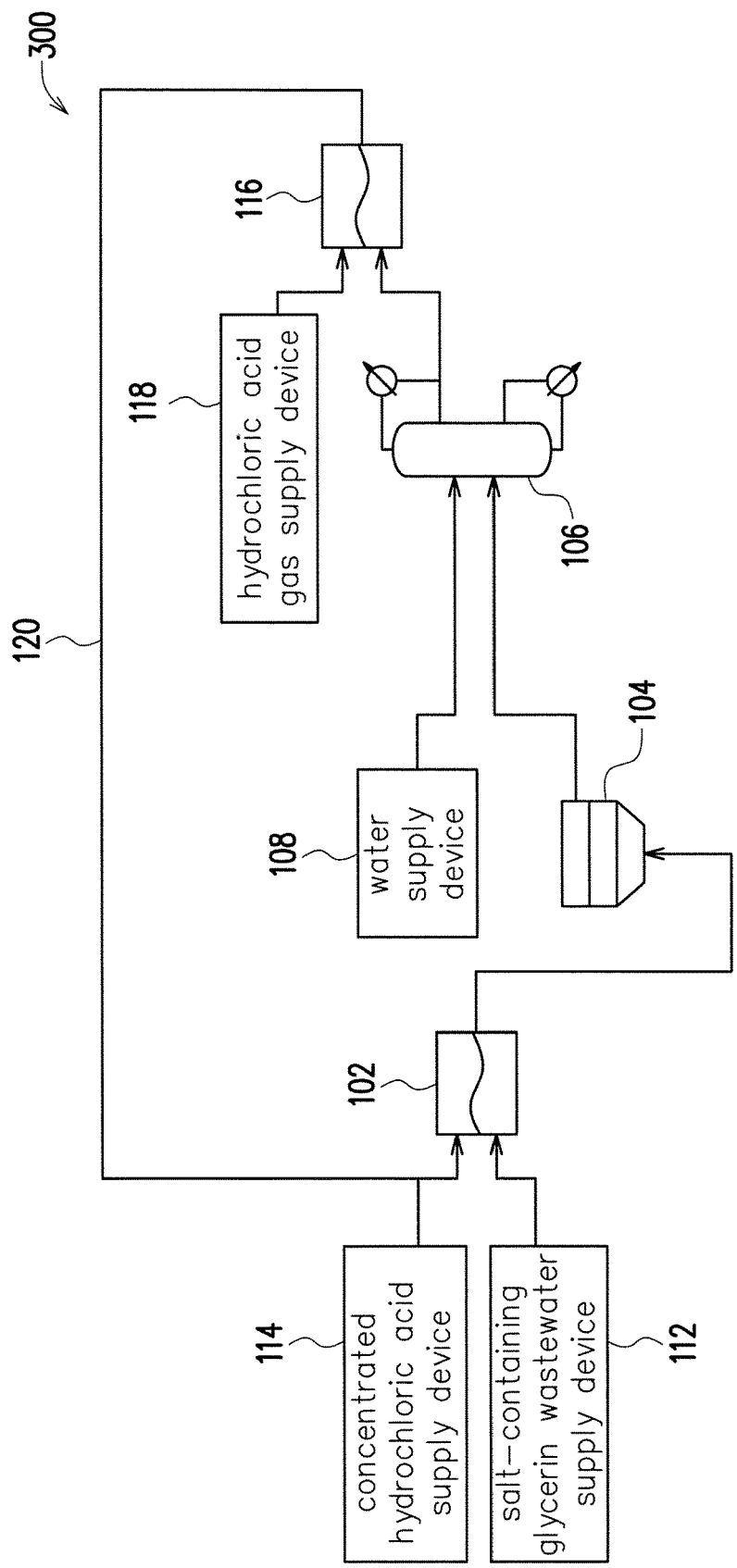
FIG. 3 is a schematic diagram of the salt-containing glycerin wastewater treating system according to another embodiment of the invention.
Figure 4:
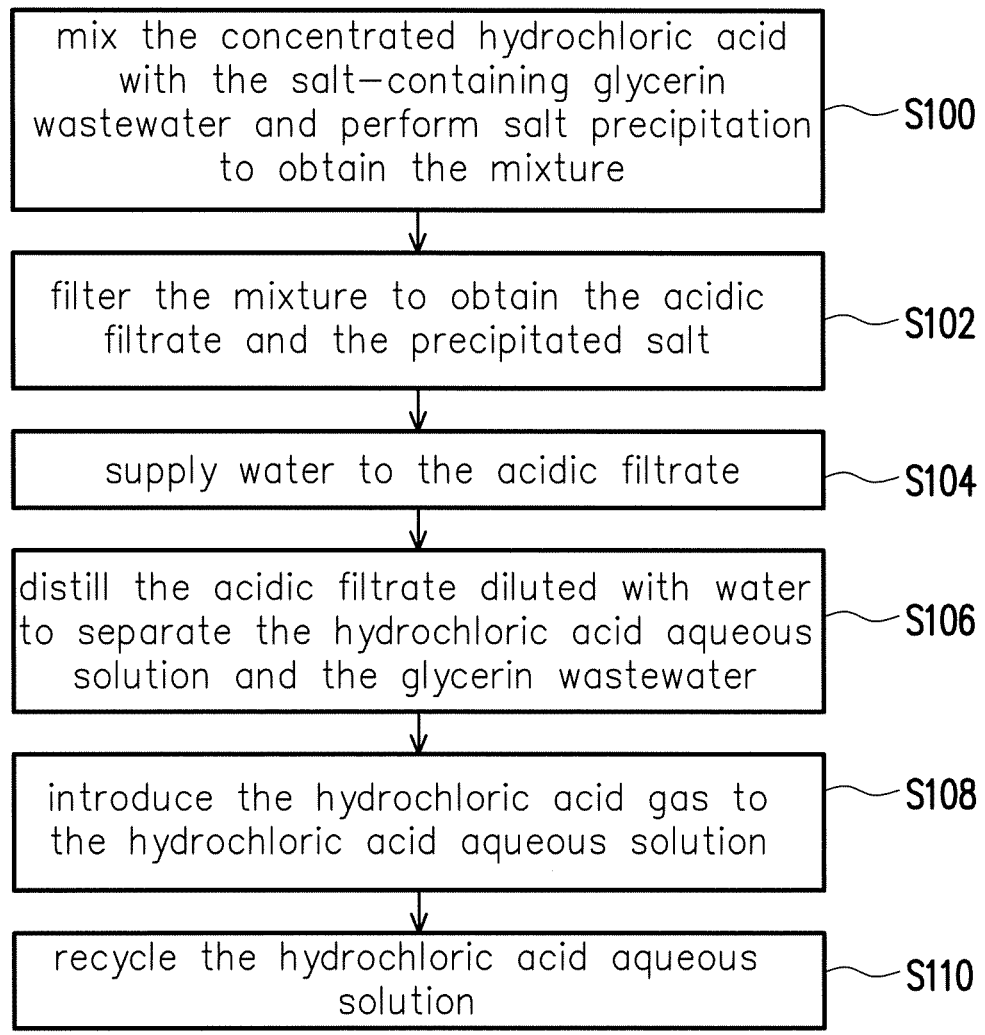
FIG. 4 is a flowchart of a salt-containing glycerin wastewater treating method according to an embodiment of the invention.

FIG. 1 is a schematic diagram of a salt-containing glycerin wastewater treating system according to an embodiment of the invention. FIG. 2 is a schematic diagram of the salt-containing glycerin wastewater treating system according to another embodiment of the invention. FIG. 3 is a schematic diagram of the salt-containing glycerin wastewater treating system according to another embodiment of the invention. FIG. 4 is a flowchart of a salt-containing glycerin wastewater treating method according to an embodiment of the invention.

Referring to FIG. 1, a salt-containing glycerin wastewater treating system 100 includes a mixing tank 102, a filtering device 104, a distillation column 106, and a water supply device 108. The salt-containing glycerin wastewater treating system 100 may further include at least one of an acidic filtrate storage tank 110, a salt-containing glycerin wastewater supply device 112, a concentrated hydrochloric acid supply device 114, a column top product storage tank 116, a hydrochloric acid gas supply device 118, and a return pipe 120. The salt-containing glycerin wastewater treating system 100 may separate a salt from salt-containing glycerin wastewater to achieve desalination.

The mixing tank 102 is adapted to mix the salt-containing glycerin wastewater with a concentrated hydrochloric acid to obtain a mixture. In the mixing tank 102, the concentrated hydrochloric acid may cause salt precipitation in the salt-containing glycerin wastewater, so as to effectively precipitate the salt from the salt-containing glycerin wastewater. A method of mixing the salt-containing glycerin wastewater with the concentrated hydrochloric acid is stirring and mixing, for example. A concentration of the concentrated hydrochloric acid is 30% to 37%, for example. An amount of the concentrated hydrochloric acid is 0.5 to 1.5 times an amount of the salt-containing glycerin wastewater, for example, so as to more effectively precipitate the salt from the salt-containing glycerin wastewater.

The filtering device 104 communicates with the mixing tank 102 and filters the mixture to obtain an acidic filtrate and a precipitated salt, so as to separate the salt from the mixture. The filtering device 104 is a press filter, for example.

The distillation column 106 communicates with the filtering device 104 and receives the acidic filtrate from the filtering device 104. The distillation column 106 may distill the acidic filtrate from the filtering device 104. In this embodiment, the acidic filtrate from the filtering device 104 may be stored in the acidic filtrate storage tank 110 first and then delivered to the distillation column 106. Nevertheless, the invention is not limited thereto.

The water supply device 108 supplies water to the acidic filtrate to obtain an acidic filtrate diluted with water. In this embodiment, the water supply device 108 may communicate with the acidic filtrate storage tank 110 that communicates between the filtering device 104 and the distillation column 106. An amount of the water supplied to the acidic filtrate is 0.25 to 1 times the amount of the salt-containing glycerin wastewater, for example.

Since the acidic filtrate received by the distillation column 106 has been diluted with water, after the acidic filtrate diluted with water is distilled, a column top product including a hydrochloric acid aqueous solution and a column bottom product including glycerin wastewater are obtained, so as to separate the hydrochloric acid aqueous solution and the glycerin wastewater from each other. Thus, the salt-containing glycerin wastewater treating system 100 is capable of effectively recycling hydrochloric acid.

The salt-containing glycerin wastewater supply device 112 communicates with the mixing tank 102 to provide the salt-containing glycerin wastewater to the mixing tank 102. The concentrated hydrochloric acid supply device 114 communicates with the mixing tank 102 to provide the concentrated hydrochloric acid to the mixing tank 102.

The column top product storage tank 116 communicates with the distillation column 106 and stores the column top product of the distillation column 106, wherein the column top product includes the hydrochloric acid aqueous solution.

The hydrochloric acid gas supply device 118 communicates with the column top product storage tank 116 to introduce a hydrochloric acid gas to the hydrochloric acid aqueous solution included in the column top product. Thus, the hydrochloric acid gas supply device 118 may adjust a concentration of the hydrochloric acid aqueous solution to facilitate recycling of the hydrochloric acid aqueous solution.

The return pipe 120 communicates between the column top product storage tank 116 and the mixing tank 102 for the hydrochloric acid aqueous solution with adjusted concentration to flow back to the mixing tank 102 for use again.

It is known from the above embodiment that, in the salt-containing glycerin wastewater treating system 100, the concentrated hydrochloric acid is used to cause salt precipitation in the salt-containing glycerin wastewater, and therefore, the salt is precipitated from the salt-containing glycerin wastewater effectively. In addition, since water is added to the acidic filtrate obtained through filtering, after the acidic filtrate diluted with water is distilled, the hydrochloric acid may be recycled effectively.

Referring to FIG. 1 and FIG. 2, a difference between a salt-containing glycerin wastewater treating system 200 of FIG. 2 and the salt-containing glycerin wastewater treating system 100 of FIG. 1 is described as follows. In the salt-containing glycerin wastewater treating system 200, the water supply device 108 may communicate with an acidic filtrate delivery pipe 202 that communicates between the filtering device 104 and the distillation column 106 to supply water to the acidic filtrate, so as to obtain the acidic filtrate diluted with water. In addition, the salt-containing glycerin wastewater treating system 200 of FIG. 2 and the salt-containing glycerin wastewater treating system 100 of FIG. 1 achieve similar effects, and identical components are assigned with the same reference numerals and thus detailed descriptions thereof are not repeated hereinafter.

Referring to FIG. 1 and FIG. 3, a difference between a salt-containing glycerin wastewater treating system 300 of FIG. 3 and the salt-containing glycerin wastewater treating system 100 of FIG. 1 is described as follows. In the salt-containing glycerin wastewater treating system 300, the water supply device 108 may directly communicate with the distillation column 106 to supply water to the acidic filtrate, so as to obtain the acidic filtrate diluted with water. In addition, the salt-containing glycerin wastewater treating system 300 of FIG. 3 and the salt-containing glycerin wastewater treating system 100 of FIG. 1 achieve similar effects, and identical components are assigned with the same reference numerals and thus detailed descriptions thereof are not repeated hereinafter.

FIG. 4 is a flowchart of a salt-containing glycerin wastewater treating method according to an embodiment of the invention. The salt-containing glycerin wastewater treating method of FIG. 4 is described hereinafter based on the salt-containing glycerin wastewater treating system 100 of FIG. 1. Nevertheless, the invention is not limited thereto. In other embodiments, the salt-containing glycerin wastewater treating method of FIG. 4 may also be performed with use of other salt-containing glycerin wastewater treating systems. Details of the connection relationship, characteristics, and efficiency of each component in the salt-containing glycerin wastewater treating system 100 have been specified above and thus are not repeated hereinafter.

Referring to FIG. 1 and FIG. 4, Step S100 is performed to mix the concentrated hydrochloric acid with the salt-containing glycerin wastewater and perform salt precipitation, so as to obtain the mixture. For example, the salt-containing glycerin wastewater supply device 112 may be used to provide the salt-containing glycerin wastewater to the mixing tank 102, and the concentrated hydrochloric acid supply device 114 may be used to provide the concentrated hydrochloric acid to the mixing tank 102, and in the mixing tank 102, the concentrated hydrochloric acid and the salt-containing glycerin wastewater are mixed. Further, in the mixing tank 102, the concentrated hydrochloric acid causes salt precipitation in the salt-containing glycerin wastewater, so as to effectively precipitate the salt from the salt-containing glycerin wastewater. The method of mixing the salt-containing glycerin wastewater with the concentrated hydrochloric acid is stirring and mixing, for example. The concentration of the concentrated hydrochloric acid is 30% to 37%, for example. The amount of the concentrated hydrochloric acid is 0.5 to 1.5 times the amount of the salt-containing glycerin wastewater, for example, so as to more effectively precipitate the salt from the salt-containing glycerin wastewater.

Step S102 is performed to filter the mixture to obtain the acidic filtrate and the precipitated salt. For example, the filtering device 104 may be used to filter the mixture to obtain the acidic filtrate and the precipitated salt for separating the salt from the mixture.

Step S104 is performed to supply water to the acidic filtrate, so as to obtain the acidic filtrate diluted with water. The amount of the water supplied to the acidic filtrate is 0.25 to 1 times the amount of the salt-containing glycerin wastewater, for example. In this embodiment, a method of supplying water to the acidic filtrate is supplying water to the acidic filtrate storage tank 110 (refer to FIG. 2). In another embodiment, the method of supplying water to the acidic filtrate may be supplying water to the acidic filtrate delivery pipe 202 (refer to FIG. 2). In other embodiments, the method of supplying water to the acidic filtrate may also be supplying water to the distillation column 106 that is used for distilling the acidic filtrate (refer to FIG. 3).

Step S106 is performed to distill the acidic filtrate diluted with water, so as to separate the hydrochloric acid aqueous solution and the glycerin wastewater from each other. For example, the distillation column 106 may be used to distill the acidic filtrate diluted with water, so as to obtain the column top product including the hydrochloric acid aqueous solution and the column bottom product including the glycerin wastewater. Thus, the salt-containing glycerin wastewater treating system 100 is capable of effectively recycling hydrochloric acid.

Step S108 may be performed selectively to introduce the hydrochloric acid gas to the hydrochloric acid aqueous solution to adjust the concentration of the hydrochloric acid aqueous solution, so as to facilitate recycling of the hydrochloric acid aqueous solution. For example, the hydrochloric acid gas supply device 118 may be used to introduce the hydrochloric acid gas to the hydrochloric acid aqueous solution stored in the column top product storage tank 116.

Step S110 may be performed selectively to recycle the hydrochloric acid aqueous solution. For example, the return pipe 120 that communicates between the column top product storage tank 116 and the mixing tank 102 may be used for the hydrochloric acid aqueous solution with adjusted concentration to flow back to the mixing tank 102 for use again.

It is known from the above embodiment that, in the salt-containing glycerin wastewater treating method, the concentrated hydrochloric acid is used to cause salt precipitation in the salt-containing glycerin wastewater, and therefore, the salt is precipitated from the salt-containing glycerin wastewater effectively. In addition, since water is added to the acidic filtrate obtained through filtering, after the acidic filtrate diluted with water is distilled, the hydrochloric acid may be recycled effectively.

EXPERIMENTAL EXAMPLE

Example 1: Salt Precipitation for the Salt-Containing Glycerin Wastewater with Use of Concentrated Hydrochloric Acid FIG. 5 is a graph showing the relationship between a ratio of the amount of concentrated hydrochloric acid to the amount of salt-containing glycerin wastewater and a salt recovery rate according to an experimental example of the invention.

Figure 5:
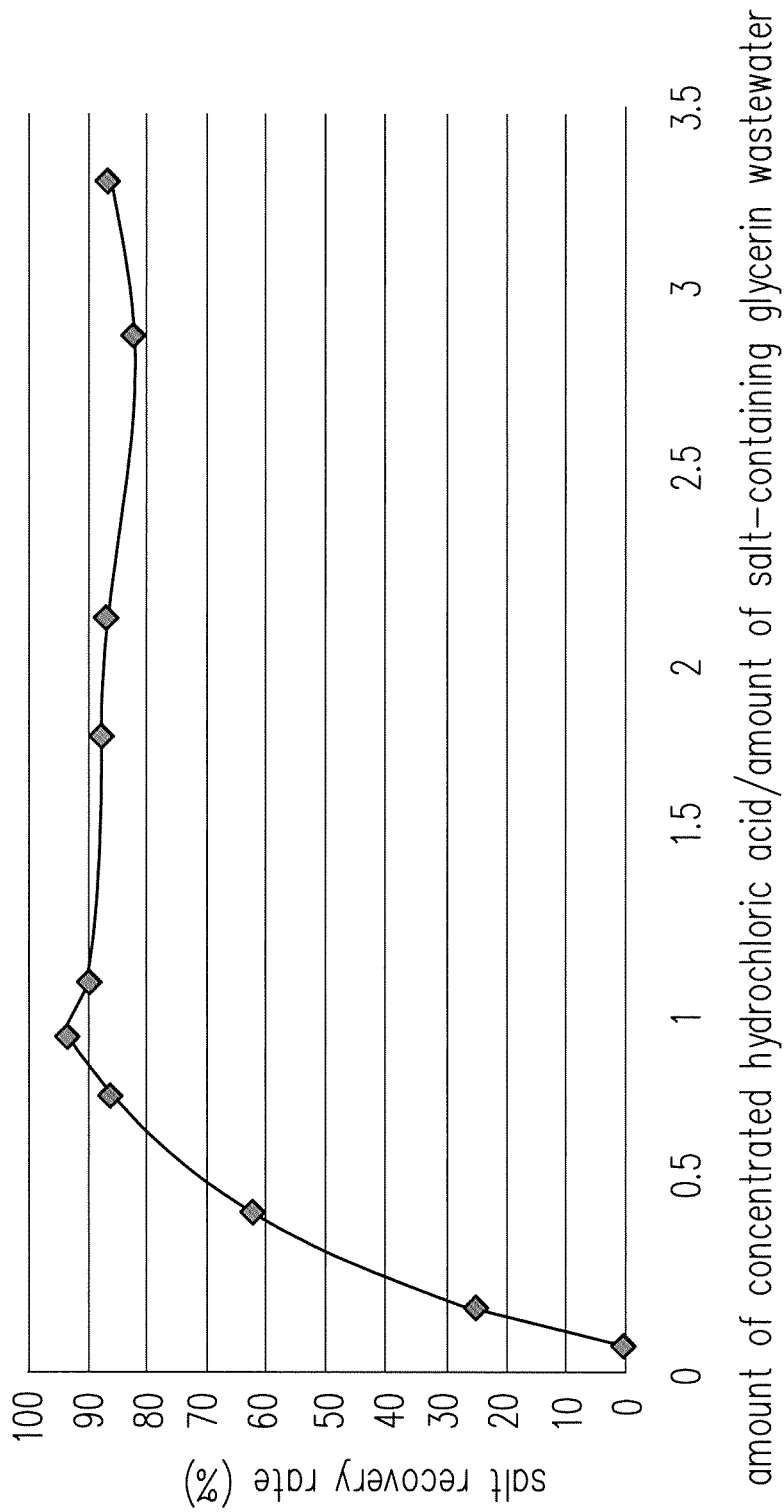
FIG. 5 is a graph showing the relationship between a ratio of the amount of concentrated hydrochloric acid to the amount of salt-containing glycerin wastewater and a salt recovery rate according to an experimental example of the invention.

Referring to FIG. 5, 37% concentrated hydrochloric acid was added to salt-containing glycerin wastewater and stirred. Concentrated hydrochloric acid in about the same amount as the salt-containing glycerin wastewater was able to precipitate 90% or more of the salt. Then, the filtering device was used to separate the precipitated salt and the salt-containing glycerin wastewater to achieve desalination.

The values at respective operating points in FIG. 5 are shown in Table 1 below.

TABLE 1

| Values at respective operating points in FIG. 5 | | | | | | | | | | |
|---|---|---|---|---|---|---|---|---|---|---|
| Amount of concentrated hydrochloric acid/amount of salt-containing glycerin wastewater | 0.1 | 0.2 | 0.4 | 0.7 | 0.9 | 1.1 | 1.7 | 2.2 | 2.8 | 3.3 |
| Salt recovery rate(%) | 0 | 25 | 62 | 87 | 94 | 90 | 88 | 87 | 82 | 87 |

Example 2: Examples of Distillation of Acidic Filtrate with/without Water (Based on Concentrated Hydrochloric Acid Amount/Wastewater Amount=1.1)

TABLE 2

Comparison between distillates obtained from acidic filtrate with/without water

| Experiment | Liquid weight (g) | Distillate (g) | Hydrochloric acid amount (g) |
|---|---|---|---|
| Amount of hydrochloric acid added initially | 55 | — | 20.35 |
| Distillation of acidic filtrate without water | 98.3 | 11.89 | 8.95 |
| Distillation of acidic filtrate with water | 144.1 | 95.8 | 20.12 |

Referring to Table 2, when the acidic filtrate obtained through filtering was distilled directly by the distillation device for recycling hydrochloric acid, only a small amount of distillate (11.89 g) and hydrochloric acid (8.95 g) were obtained. The recycling was inefficient. On the other hand, when water (50 g) was added to dilute the acidic filtrate obtained through filtering for distillation, 90% or more of the distillate (95.8 g) and hydrochloric acid (20.12 g) were recycled, and the hydrochloric acid gas may be introduced to the recycled hydrochloric acid aqueous solution to obtain concentrated hydrochloric acid for use again.

To sum up, in the salt-containing glycerin wastewater treating system and method as described in the above embodiments, concentrated hydrochloric acid is used to cause salt precipitation in the salt-containing glycerin wastewater, so as to precipitate salt from the salt-containing glycerin wastewater effectively. In addition, water is added to the acidic filtrate obtained through filtering, and then the acidic filtrate diluted with water is distilled, so as to recycle the hydrochloric acid effectively.

It will be apparent to those skilled in the art that various modifications and variations can be made to the disclosed embodiments without departing from the scope or spirit of the invention. In view of the foregoing, it is intended that the invention covers modifications and variations of this disclosure provided that they fall within the scope of the following claims and their equivalents.

What is claimed is:

1. A salt-containing glycerin wastewater treating system, comprising:
   a mixing tank adapted to mix salt-containing glycerin wastewater with a concentrated hydrochloric acid to obtain a mixture;
   a filtering device communicating with the mixing tank and filtering the mixture to obtain an acidic filtrate and a precipitated salt;
   a distillation column communicating with the filtering device and receiving the acidic filtrate from the filtering device;
   a water supply device supplying water to the acidic filtrate;
   a column top product storage tank that communicates with the distillation column and stores a column top product of the distillation column, wherein the column top product comprises a hydrochloric acid aqueous solution;
   a return pipe that communicates between the column top product storage tank and the mixing tank; and
   a hydrochloric acid gas supply device that communicates with the column top product storage tank.

2. The salt-containing glycerin wastewater treating system according to claim 1, further comprising:
   a salt-containing glycerin wastewater supply tank communicating with the mixing tank; and
   a concentrated hydrochloric acid supply tank communicating with the mixing tank.

3. The salt-containing glycerin wastewater treating system according to claim 1, wherein the water supply tank communicates with an acidic filtrate storage tank that communicates between the filter and the distillation column, communicates with an acidic filtrate delivery pipe that communicates between the filter and the distillation column, or directly communicates with the distillation column.

4. The salt-containing glycerin wastewater treating system according to claim 1, further comprising a hydrochloric acid gas supply tank that communicates with the column top product storage tank.

5. A salt-containing glycerin wastewater treating method, comprising:
   mixing a concentrated hydrochloric acid with salt-containing glycerin wastewater and performing salt precipitation to obtain a mixture, wherein a concentration of the concentrated hydrochloric acid is 30% to 37%;
   filtering the mixture to obtain an acidic filtrate and a precipitated salt;
   supplying water to the acidic filtrate; and
   distilling the acidic filtrate diluted with the water to separate a hydrochloric acid aqueous solution and glycerin wastewater by a distillation column, wherein the hydrochloric acid aqueous solution is stored in a column top product storage tank, and a return pipe communicates between the column top product storage tank and the mixing tank; and introducing a hydrochloric acid gas to the hydrochloric acid aqueous solution in the column top product storage tank.

6. The salt-containing glycerin wastewater treating method according to claim 5, wherein an amount of the concentrated hydrochloric acid is 0.5 to 1.5 times an amount of the salt-containing glycerin wastewater.

7. The salt-containing glycerin wastewater treating method according to claim 5, wherein an amount of the water supplied to the acidic filtrate is 0.25 to 1 times an amount of the salt-containing glycerin wastewater.

8. The salt-containing glycerin wastewater treating method according to claim 5, wherein a method of supplying the water to the acidic filtrate comprises supplying the water to an acidic filtrate storage tank, supplying the water to an acidic filtrate delivery pipe, or directly supplying the water to a distillation column that is adapted to distill the acidic filtrate.

9. The salt-containing glycerin wastewater treating method according to claim 5, further comprising introducing a hydrochloric acid gas to the hydrochloric acid aqueous solution.

10. The salt-containing glycerin wastewater treating method according to claim 5, further comprising recycling the hydrochloric acid aqueous solution.

* * * * *